(12) United States Patent
Kuehl et al.

(10) Patent No.: US 6,945,123 B1
(45) Date of Patent: Sep. 20, 2005

(54) GAS FLOW SENSOR HAVING REDUNDANT FLOW SENSING CAPABILITY

(75) Inventors: Kenneth J. Kuehl, Oregon, WI (US); Kristen E. Nelson Mock, Lake Mills, WI (US); Donald C. Meyferth, Sun Prairie, WI (US)

(73) Assignee: The General Electric Company, Schenectady, NY (US)

( * ) Notice: Subject to any disclaimer, the term of this patent is extended or adjusted under 35 U.S.C. 154(b) by 0 days.

(21) Appl. No.: 10/878,949

(22) Filed: Jun. 28, 2004

(51) Int. Cl.[7] .............................................. G01F 1/34
(52) U.S. Cl. .................................................. 73/861.42
(58) Field of Search .................... 73/861.04, 23.31, 73/861.65, 204.22, 861.53, 861.52, 861.42

(56) References Cited

U.S. PATENT DOCUMENTS

| | | | | |
|---|---|---|---|---|
| 4,366,709 A | * | 1/1983 | Eiermann et al. | ......... 73/204.22 |
| 4,856,344 A | * | 8/1989 | Hunt | ...................... 73/861.04 |
| 5,033,312 A | * | 7/1991 | Stupecky | ................. 73/861.53 |
| 5,099,697 A | * | 3/1992 | Agar | ...................... 73/861.04 |
| 5,365,795 A | * | 11/1994 | Brower, Jr. | .............. 73/861.65 |
| 5,379,650 A | | 1/1995 | Koeoed et al. | |
| 5,501,099 A | * | 3/1996 | Whorff | ...................... 73/29.01 |
| 5,535,633 A | | 7/1996 | Kofoed et al. | |
| 6,422,092 B1 | * | 7/2002 | Morrison et al. | ........ 73/861.04 |
| 6,460,400 B1 | * | 10/2002 | Ichikawa | .................... 73/23.31 |
| 6,470,741 B1 | | 10/2002 | Fathollahzadeh | |
| 6,658,946 B2 | | 12/2003 | Lipscomb et al. | |
| 6,681,643 B2 | * | 1/2004 | Heinonen | ................ 73/861.52 |

\* cited by examiner

*Primary Examiner*—Edward Lefkowitz
*Assistant Examiner*—Jewel V. Thompson

(57) ABSTRACT

A sensor for redundantly measuring gas flow has a housing suitable for being interposed in a gas flow conduit. The housing has an orifice through which the gas to be measured flows. A gas flow measuring, hot wire anemometer is positioned in the housing proximate to the orifice for providing a first measurement of the gas flow in the conduit. A first absolute pressure sensor measures gas pressure downstream of the orifice. The first pressure sensor may provide pressure compensation to the anemometer. A second absolute pressure sensor measures gas pressure upstream of the orifice. The first pressure sensor may be further used with the second pressure sensor to obtain a differential pressure measurement providing a further measurement of the gas flow in the conduit that is redundant to that of the anemometer.

22 Claims, 3 Drawing Sheets

GAS FLOW SENSOR HAVING REDUNDANT FLOW SENSING CAPABILITY

The present invention relates to gas flow sensors having redundant flow sensing capabilities. While not so limited, such a sensor finds particular utility in medical equipment for measuring gas flow rates in anesthesia machines and ventilators and is described in that context, below.

BACKGROUND OF THE INVENTION

Anesthesia machines and ventilators provide breathing gases to a patient in a clinical setting. These breathing gases are formed by mixing gases from supplies of compressed gas such as air, oxygen, and nitrous oxide. To insure proper concentrations of the gases, flow sensors are needed in supply lines for the gases to measure the flow rates of the different, component, gases forming the breathing gases given to the patient. Many types of flow sensors are available for this application including, but not limited to, differential pressure, hot wire anemometer, turbine, and ultrasound sensors.

While these types of flow sensors can provide accurate measurement of gas flow in an anesthesia machine or ventilator, an essential problem exists in such an application of protecting the patient against a fault or failure of a flow sensor. U.S. Pat. No. 6,658,946 to Lipscomb shows a flow rate measurement system that uses a second flow rate sensor to serve as a redundant flow rate measurement device that operates on a different physiological parameter. However, the addition of another stand-alone flow sensor increases the complexity, size, and cost of the flow sensing components. Also, an additional stand-alone flow sensor may introduce an additional pressure drop in the gas supply line impeding or preventing proper operation of the apparatus.

SUMMARY OF THE INVENTION

It is, therefore, the object of the present invention to provide a redundant gas flow sensing system having small size and low cost thereby to overcome the current shortcomings in providing highly reliable and certain flow sensing in critical applications such as those involving patient care.

It is a further object of the present invention to provide a gas flow sensor in which the measurement of different physical phenomena is used to provide the redundant sensing and which is suitable for implementation with multiple gases.

A still further object of the present invention is to provide a gas flow sensor that employs a pressure sensor providing pressure compensation for one flow measurement means as an element in other redundant, flow measurement means.

The present invention obtains redundant flow sensing capabilities with small size and cost by providing a flow sensor having a housing suitable for being interposed in a conduit, the gas flow in which is to be measured. The housing has an orifice through which the gas to be measured flows. A gas flow measuring hot wire anemometer is positioned in the housing proximate the orifice for providing a measurement of the gas flow in the conduit. A first absolute pressure sensor is located to measure gas pressure downstream, of the orifice. The first pressure sensor provides pressure compensation to the gas flow measurement of the anemometer.

In accordance with the invention, a second absolute pressure sensor is located for measuring gas pressure upstream of the orifice. The first and second pressure sensors are coupled to a differential pressure measurement means for providing a measurement of the gas flow in the conduit that is redundant to that of the anemometer.

The gas flow sensor of the present invention measures the gas flow using two different physical phenomena. The first is that of the hot wire anemometer. The pressure sensors use a second physical phenomenon, the difference in pressure as the gas passes through the orifice. This is desirable because it increases the reliability of the redundant measurement of the gas flow rate. This invention is also suitable to measure the flow rates in multiple gas supply conduits connected to a common mixing conduit. Only one downstream pressure sensor in the mixing conduit is needed to measure the differential pressure for any number of gas supply conduits.

The gas flow sensor of the present invention provides accurate measurements with compensation for changes in temperature and/or atmospheric or system pressures. The temperature sensor in the anemometer flow sensor also provides temperature compensation for the redundant differential pressure flow measurement. Additionally, the use of two absolute pressure transducers avoids the need for internal pressure compensation because the gas flow measurement is a relative differential pressure measurement.

BRIEF DESCRIPTION OF THE DRAWINGS

The drawings illustrate the best mode presently contemplated for carrying out the invention.

In the drawings.

DETAILED DESCRIPTION OF THE INVENTION

Figure 1:
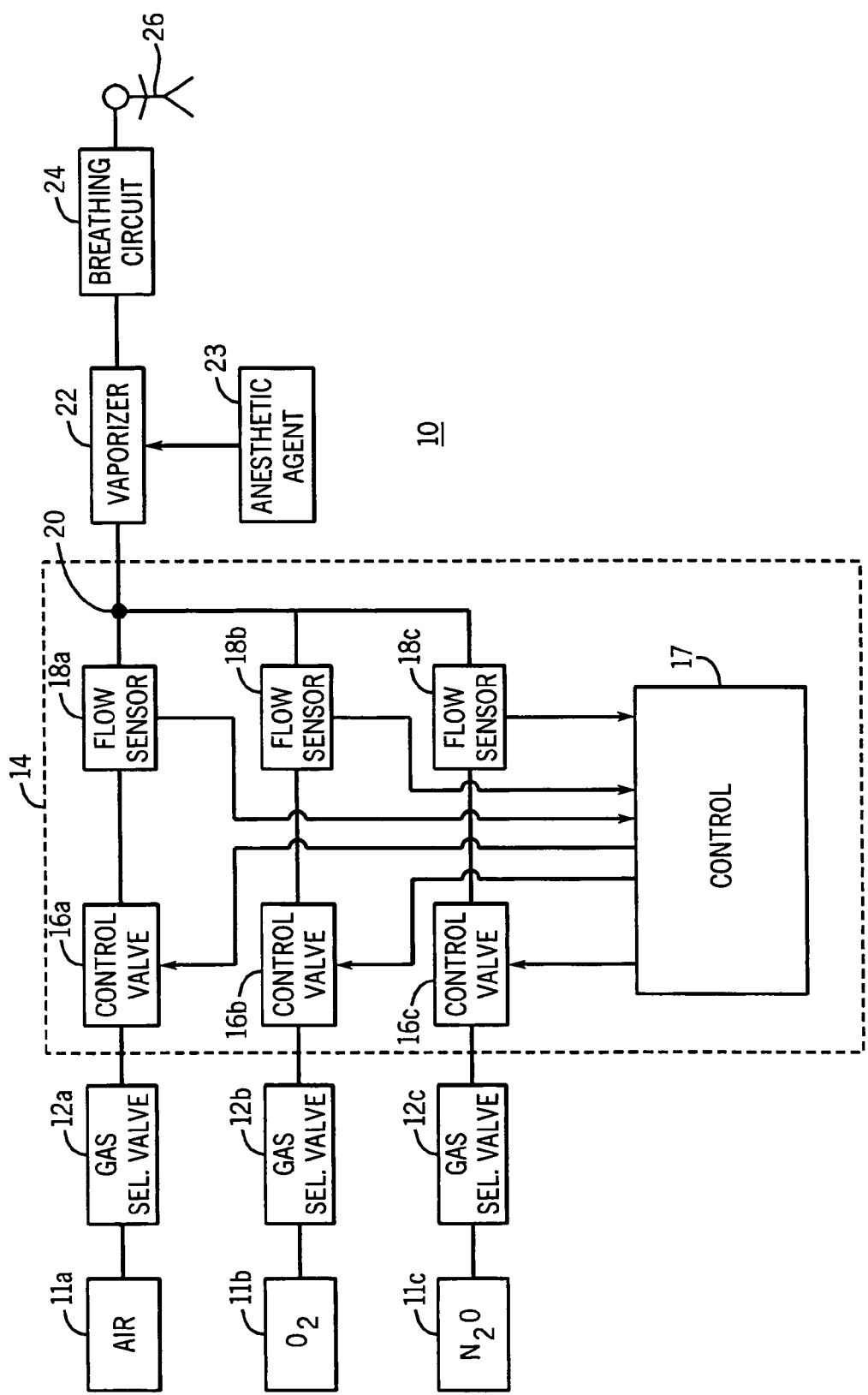
FIG. 1 is a schematic view of exemplary apparatus in which the redundant gas flow sensor of the present invention may be used.

The redundant gas flow sensor of the present invention is shown in FIG. 1 in an application in which breathing gases are being provided to a patient in a medical setting. FIG. 1 shows a block diagram of an anesthesia machine 10 which is typically supplied with a plurality of medical gases, such as air, oxygen, and nitrous oxide, from pressurized sources 11a, 11b, 11c, respectively. The sources are connected to gas selector valves 12a, 12b, and 12c and to a gas mixer 14. For each of the gases, the gas mixer 14 includes a control valve, control valves 16a, 16b, and 16c, and a flow sensor 18, flow sensors 18a, 18b, and 18c, which may comprise the redundant flow sensor of the present invention. Control valves 16a, 16b, and 16c and flow sensors 18a, 18b, and 18c are connected to control 17 that operates the valves responsive to the gas flows sensed by the sensors and to other inputs. The gases from sources 11a, 11b, and 11c are combined to form a mixed gas at mixed gas outlet 20. The mixed gas flows to vaporizer 22 where an anesthetic agent is added to the mixed gas from source 23. The anesthetic agent and mixed gas combination enters the breathing circuit 24 and is delivered to the patient 26 as the breathing gases for the patient.

Figure 2:
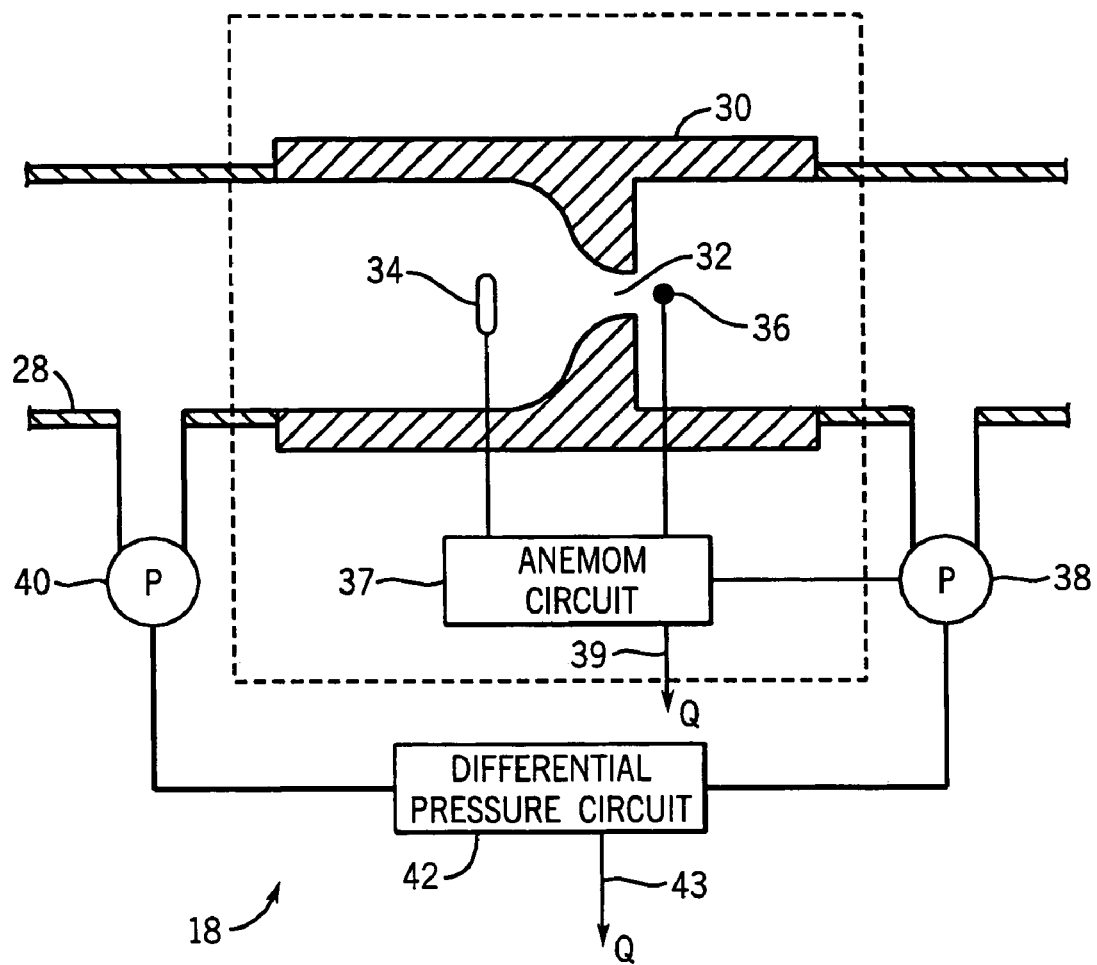
FIG. 2 is a cross sectional view showing the redundant flow sensor.

FIG. 2 shows the cross sectional view of the redundant gas flow sensor 18 of the present invention which may comprise a flow sensor 18a, 18b, 18c shown in FIG. 1. Flow sensor 18 is inserted in a gas conduit 28 by appropriate connectors formed in housing 30. Housing 30 includes an integral orifice 32. Orifice 32 narrows the cross-sectional area of supply line 28 and creates a jet of gas flow and a pressure drop through it.

Hot wire anemometer 36 is located proximally and downstream of orifice 32. Temperature sensor 34 is located upstream of orifice 32. Anemometer 36 and temperature sensor 34 are connected to flow measurement circuitry 37 that measures the flow of gas through supply line 28 and provides an output signal 39 indicative of same. Housing 30, anemometer 36, temperature sensor 34, and circuitry 37 may comprise the flow sensor sold by TSI Incorporated of Shoreview, Minn. under the designation Series 8402000.

Downstream from flow sensor 36 is a first (downstream) absolute pressure sensor 38. An absolute pressure sensor measures pressure against a vacuum or zero pressure. This pressure sensor provides pressure compensation due to changes in atmospheric pressure and in back pressure from the vaporizer, breathing circuit, and patient and is connected to measurement circuitry 37 for this purpose.

In accordance with the present invention, upstream from orifice 32 is a second (upstream) absolute pressure sensor 40. Downstream pressure sensor 38 and upstream pressure sensor 40 are connected to differential pressure circuit flow measurement circuit 42. The circuit 42 determines the differential pressure across orifice 32 and the gas flow rate through conduit 28 based upon differential pressure and provides an output 43 indicative of same. The use of absolute pressure sensors for pressure sensors 38 and 40 allows for the elimination of the zeroing valves normally needed by a differential pressure circuit when the pressures measured are relative pressures.

The operation of the redundant gas flow sensor 18 of the present invention is as follows. As gas flows in supply line 28 and housing 30, second pressure transducer 40 measures the absolute pressure of the gas upstream of orifice 32. As the gas goes through orifice 32, the cross-sectional area of conduit 28 is reduced, thereby creating a pressure drop and a focused jet of gas flow. This pressure drop is detected by first pressure sensor 38 which measures the absolute pressure of the system downstream from the orifice 32. Anemometer 36 has a resistance wire or other component that is heated by current from measurement circuitry 37. The gas of the focused jet created by orifice 32 cools the hot wire of anemometer 36, altering its resistance and causing circuitry 37 to produce a measurement 39 of the gas flow in supply line 28. This measurement of flow is compensated for changes in the gas temperature by temperature sensor 34 and the absolute pressure reading of the first (downstream) pressure transducer 38 compensates the measurement for changes in atmosphere pressure and system back pressure due to the vaporizer 22, breathing circuit 24, and patient 26.

The foregoing provides a first measurement of gas flow performed by the redundant flow sensor, a measurement of flow based upon the cooling properties of the gas as it moves past the hot wire anemometer. A second, or redundant, measurement of flow is performed by the differential pressure circuit 42 by comparing the absolute pressures of the first (downstream) pressure transducer 38 and second (upstream) pressure transducer 40. This measurement is compensated for changes in temperature by temperature sensor 34. This measurement of flow relies upon a different physiological measurand, i.e. differential pressure, than that of the hot wire anemometer.

Figure 3:
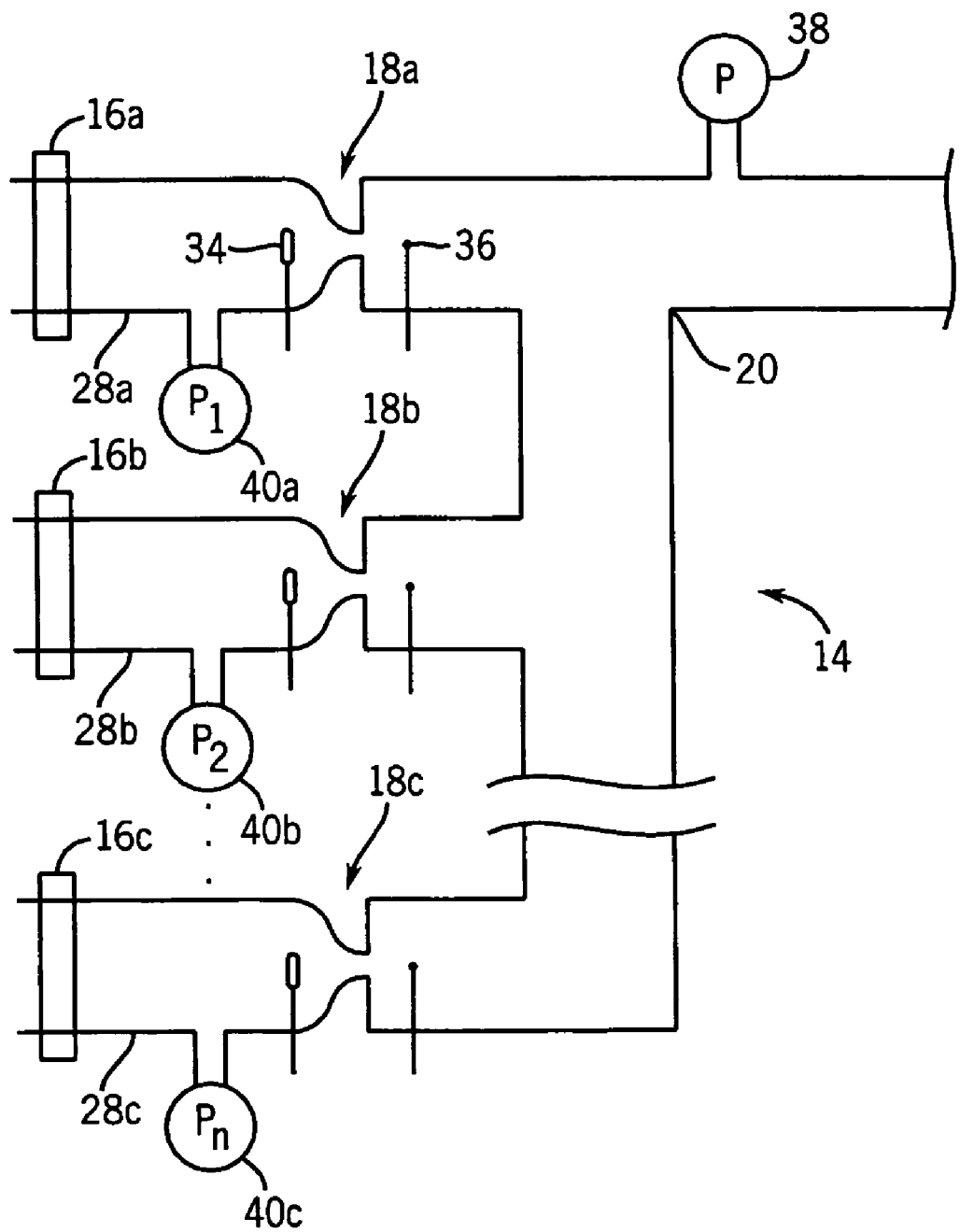
FIG. 3 is a cross sectional view showing the redundant flow sensor in a gas mixer with a plurality of gas conduits.

FIG. 3 further shows the gas mixer 14 of FIG. 1. As in FIG. 1, the flow rates in each conduit 28a, 28b, and 28c are controlled by a control valve and measured by a redundant gas flow sensor 18a, 18b, and 18c, respectively, before being combined in the mixed gas outlet 20. It will be appreciated from FIG. 3 that the flow sensing arrangement uses a plurality of second (upstream) pressure sensors 40a, 40b, and 40c but only a single first (downstream) pressure sensor 38, located after the medical gases have been mixed at the mixed gas outlet 20. This design that employs only a single downstream pressure sensor allows for the reduction of cost for the implementation of the redundant flow sensor 18 on multiple supply lines of medical gases.

It is recognized that other equivalents, alternatives, and modifications aside from those expressly stated, are possible and within the scope of the appended claims.

What is claimed is:

1. A sensor for redundantly measuring the amount of gas flow in a conduit having a gas flow path and for providing a pair of output signals from the sensor, each of which comprises an indication of the amount of gas flow occurring in the conduit, said sensor comprising:
    a housing suitable for being interposed in the conduit said housing having an orifice through which the gas, the flow of which is to be measured, flows;
    an anemometer positioned proximate to said orifice for providing a first output signal indicative of a first measurement of the amount of gas flow in the conduit;
    a first pressure sensor positioned along said gas flow path for measuring gas pressure downstream of said anemometer;
    a second pressure sensor positioned along said gas flow path for measuring gas pressure upstream of said anemometer; and
    a differential pressure measurement means coupled to said first and second pressure sensors for providing a second output signal indicative of a second measurement of the amount of gas flow in the conduit that is redundant to that of said first output signal.

2. The redundant gas flow sensor according to claim 1 wherein said anemometer is a hot-wire anemometer.

3. The redundant gas flow sensor according to claim 2 including gas temperature measuring means for temperature compensating said hot-wire anemometer.

4. The redundant gas flow sensor according to claim 1 including gas temperature measuring means for temperature compensating said differential pressure measurement means.

5. The redundant gas flow sensor according to claim 3 wherein said temperature measuring means temperature compensates said differential pressure measurement means.

6. The redundant gas flow sensor according to claim 5 wherein a pressure sensor downstream of said orifice pressure compensates said hot wire anemometer.

7. The redundant gas flow sensor according to claim 6 wherein said downstream pressure sensor is said first pressure sensor.

8. The redundant gas flow sensor according to claim 1 wherein said pressure sensors are absolute pressure sensors.

9. The redundant gas flow sensor according to claim 1 for redundantly measuring gas flows in a plurality of gas flow conduits connected to a mixed gas conduit, each of said gas flow conduits having a housing with an orifice and anemometer interposed therein, a second pressure sensor being positioned along the flow path in each of said conduits upstream of the orifice, and a single first pressure sensor being coupled to said mixed gas conduit downstream of the orifices in said housings.

10. The redundant gas flow sensor according to claim 9 wherein the single downstream pressure sensor also provides the pressure compensation for the anemometers in said housings.

11. The redundant gas flow sensor according to claim 9 wherein said anemometers are a hot-wire anemometers.

12. A medical apparatus gas flow sensor for redundantly measuring the amount of gas flow in a medical apparatus, conduit having a gas flow path, said sensor providing a pair of output signals, each of which comprises an indication of the amount of gas flowing in the conduit, said sensor comprising:
- a housing suitable for being interposed in the conduit of the medical apparatus, said housing having an orifice through which the gas, the flow of which is to be measured, flows;
- an anemometer positioned proximate to said orifice for providing a first output signal indicative of a first measurement of the amount of gas flow in the conduit;
- a first pressure sensor positioned along said gas flow path for measuring gas pressure downstream of said anemometer;
- a second pressure sensor positioned along said gas flow path for measuring gas pressure upstream of said anemometer; and
- a differential pressure measurement means coupled to said first and second pressure sensors for providing a second output signal indicative of a second measurement of the amount of gas flow in the conduit that is redundant to that of said first output signal.

13. The redundant medical apparatus gas flow sensor according to claim 12 wherein said anemometer is a hot-wire anemometer.

14. The redundant medical apparatus gas flow sensor according to claim 13 including gas temperature measuring means for temperature compensating said hot-wire anemometer.

15. The redundant medical apparatus gas flow sensor according to claim 12 including gas temperature measuring means for temperature compensating said differential pressure measurement means.

16. The redundant medical apparatus gas flow sensor according to claim 14 wherein said temperature measuring means temperature compensates said differential pressure measurement means.

17. The redundant medical apparatus gas flow sensor according to claim 16 wherein a pressure sensor downstream of said orifice pressure compensates said hot wire anemometer.

18. The redundant medical apparatus gas flow sensor according to claim 17 wherein said downstream pressure sensor is said first pressure sensor.

19. The redundant medical apparatus gas flow sensor according to claim 12 wherein said pressure sensors are absolute pressure sensors.

20. The redundant medical apparatus gas flow sensor according to claim 12 for redundantly measuring gas flows in a medical apparatus having a plurality of gas flow conduits connected to a mixed gas conduit, each of said gas flow conduits having a housing with an orifice and anemometer interposed therein, a second pressure sensor being positioned along the flow path in each of said conduits upstream of the orifice, and a single first pressure sensor being coupled to said mixed gas conduit downstream of the orifices in said housings.

21. The redundant medical apparatus gas flow sensor according to claim 20 wherein the single downstream pressure sensor also provides the pressure compensation for the anemometers in said housings.

22. The redundant medical apparatus gas flow sensor according to claim 20 wherein said anemometers are a hot-wire anemometers.

* * * * *